(12) United States Patent
Larsen et al.

(10) Patent No.: US 9,642,963 B2
(45) Date of Patent: May 9, 2017

(54) REVOLVING NEEDLE MAGAZINE

(71) Applicant: Novo Nordisk A/S, Bagsvaerd (DK)

(72) Inventors: Andre Larsen, Dragor (DK); Jesper P. Windum, Hilleroed (DK)

(73) Assignee: Novo Nordisk A/S, Bagsvaerd (DK)

( * ) Notice: Subject to any disclaimer, the term of this patent is extended or adjusted under 35 U.S.C. 154(b) by 134 days.

(21) Appl. No.: 14/385,906

(22) PCT Filed: Jan. 21, 2013

(86) PCT No.: PCT/EP2013/051002
§ 371 (c)(1),
(2) Date: Sep. 17, 2014

(87) PCT Pub. No.: WO2013/139497
PCT Pub. Date: Sep. 26, 2013

(65) Prior Publication Data
US 2015/0025469 A1    Jan. 22, 2015

Related U.S. Application Data

(60) Provisional application No. 61/616,665, filed on Mar. 28, 2012.

(30) Foreign Application Priority Data

Mar. 22, 2012  (EP) .................................... 12160756

(51) Int. Cl.
*A61M 5/00* (2006.01)
*A61M 5/32* (2006.01)

(52) U.S. Cl.
CPC ....... *A61M 5/002* (2013.01); *A61M 2005/004* (2013.01); *A61M 2005/3267* (2013.01)

(58) Field of Classification Search
CPC .......... A61M 5/002; A61M 2005/3267; A61M 2005/004
See application file for complete search history.

(56) References Cited

FOREIGN PATENT DOCUMENTS

| CN | 201572390 U | 9/2010 |
|---|---|---|
| EP | 2420272 A1 | 2/2012 |
| EP | 2428236 A1 | 3/2012 |
| WO | 0193927 A1 | 12/2001 |
| WO | 2009/016161 A1 | 2/2009 |
| WO | 2010048753 A1 | 5/2010 |

*Primary Examiner* — Bradley Osinski
(74) *Attorney, Agent, or Firm* — Wesley Nicolas

(57) ABSTRACT

A needle magazine (1, 100) attachable to an injection device containing a liquid drug and which magazine (1, 100) comprises a main part (10, 110) and revolving part (20, 120) which can be rotated to bring a selected needle cannula (35, 135) into an injection position.
The magazine (1, 100) is provided with a centrally located tube (13, 113) for penetrating into the injection device and has an internal conduit (14, 114, 115) for guiding the liquid drug from the tube (13, 113) and to a peripheral area of the magazine (1, 100). In this peripheral area a plurality of needle cannulae (35, 135) are provided which needle cannulae (35, 135) successively can be brought into liquid communication with the liquid drug in the conduit (14, 114, 115) by axial movement of the revolving part (20, 120).

8 Claims, 4 Drawing Sheets

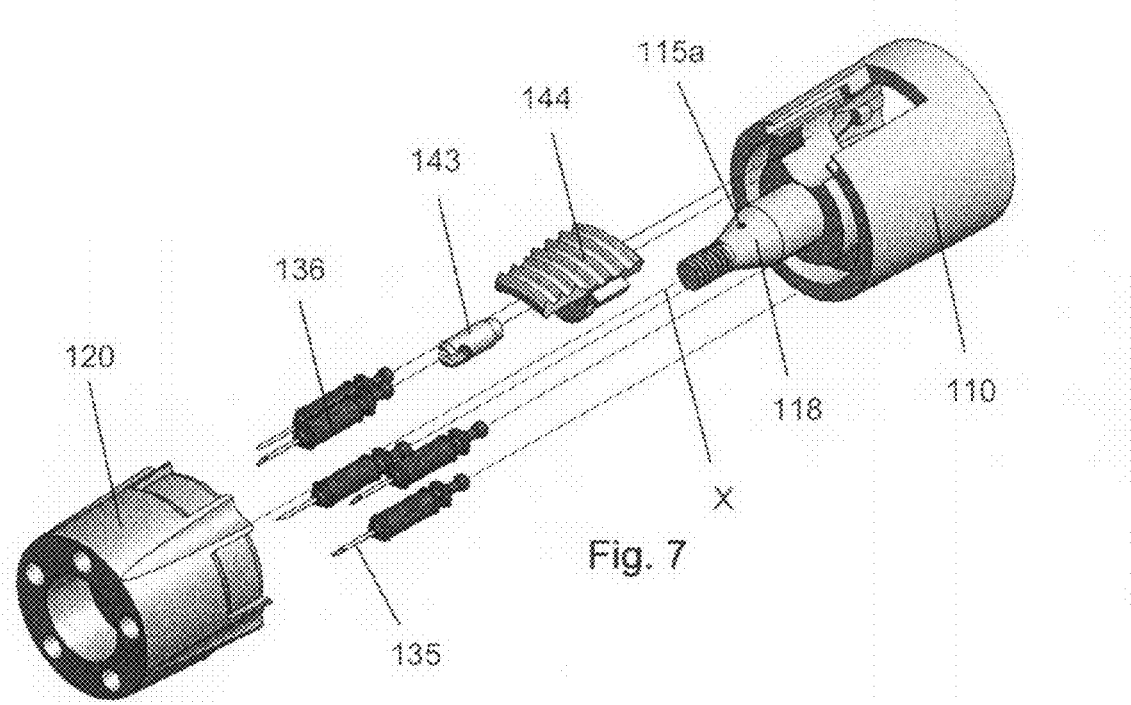
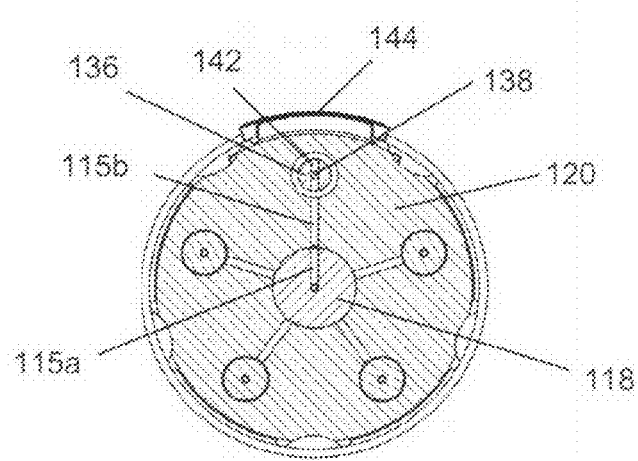

REVOLVING NEEDLE MAGAZINE

CROSS-REFERENCE TO RELATED APPLICATIONS

This application is a 35 U.S.C. §371 National Stage application of International Application PCT/EP2013/051002 (published as WO 2013/139497), filed Jan. 21, 2013, which claimed priority of European Patent Application 12160756.8, filed Mar. 22, 2012; this application claims priority under 35 U.S.C. §119 of U.S. Provisional Application 61/616,665; filed Mar. 28, 2012.

THE TECHNICAL FIELD OF THE INVENTION

The invention relates to a needle magazine for holding a plurality of needle cannulae. The needle magazine is attachable to an injection device such that each needle cannula in the plurality can be successively used to perform an injection of a liquid drug contained in the injection device.

DESCRIPTION OF RELATED ART

People suffering from diabetes have to inject themselves with insulin at a daily basis. For this purpose a great number of different injection devices have been developed over the last 35 years. The typical diabetes patient will require injections of insulin several times during the course of a day. In order to facilitate such injections the patient will need a number of injection needles and in order to prevent skin infections it is recommended to use a new sterile needle assembly for each new injection.

A prior art pen needle unit for a needle based injection system is disclosed in ISO 11608 (Needle-based injection systems for medical use, part 2, Needles), and comprises a needle cannula which is mounted in a hub. The needle cannula has an injection part which enters the body of the user during injection and a cartridge part which enters the cartridge contained in the injection device when the pen needle assembly is connected to the injection device. The pen needle assembly is usually delivered to the user ready-to-use in a sterile container which has an open proximal end sealed by a protective sheet being impermeable to germs and the like. Further, the patient end of the needle cannula is often covered by a removable inner cap. The hub usually has connecting means located on its interior side making it possible to connect the hub to the injection device.

Pen needle units for injection systems are usually delivered in carton boxes containing 100 pen needle units and a random number of those are carried around by the user loosely in their pockets, purses or briefcases. To overcome the problem of carrying loose pen needle units, a great number of different magazines for storing and carrying pen needle units have been developed over the years.

Instead of only having one needle cannulae provided on the injection device at the time it has also been suggested to provide a needle magazine to be attached directly on the injection device and holding a plurality of needle cannulae. This plurality of needle cannulae is usually located in a circular alignment in the periphery of the needle magazine.

One such needle magazine is disclosed in WO 2001/93927. In this needle magazine a plurality of needle cannulae positioned in a circular alignment in the periphery area of the needle magazine can be moved axially to penetrate into the cartridge in the injection device containing the liquid drug. A major drawback is however, that the cartridge also has to be positioned in the peripheral area of the needle magazine in order for the needle cannula to penetrate the cartridge during its axial movement.

In general injection devices for self-treatment of e.g. diabetes contains a cartridge holding the liquid drug. This cartridge is usually made from glass or polymer. A well-known variant of injection devices is the pen systems. These so-called pen systems comprise a pen shaped injection device in which the cartridge stretches along the centre line of the tubular oblong pen. The pen needle assembly is attached to the distal end of the pen-shaped injection device and penetrates through the centre of the often circular septum of the cartridge thereby creating a liquid communication channel between the interior of the cartridge and the distal pointed end of the lumen of the needle cannula. An example of such pen system is given in WO 2009/016161, in FIG. 1.

WO 09/016161 further discloses a needle magazine in which each individual needle cannulae pivots from the peripheral area to the central area of the needle magazine such that each needle successively is brought into axial alignment with the centrally located cartridge. However, this solution is rather cumbersome as it requires a high number of movable bits and parts to move each individual needle cannulae radially.

DESCRIPTION OF THE INVENTION

Having regard to the above identified prior art needle magazines, it is an object of the present invention to provide a needle magazine which is attachable to an injection device and preferably to a pen-shaped injection device having a centrally located cartridge containing the liquid drug and which needle magazine has a simple complexity with only a few movable parts.

It is especially an object of the present invention to provide a needle magazine that are small in size and easy in use, and which can be carried around attached to a well-known injection device such as e.g. a pen system.

The invention is defined in claim 1.

Accordingly in one aspect of the present invention a needle magazine is attachable to an injection device through coupling means such as threads, bayonet or the like. Alternatively the needle magazine can be provided as an integral part of an injection device or integral with a part of an injection device such as a cartridge. The needle magazine comprises:
  a main part attachable to the injection device, and
  a revolving part which is rotatable mounted in relation to the main part.

The main part is provided with a proximally pointing tube which penetrates into the injection device and through which the injection device feeds the liquid drug to be injected. This tube can be formed as a separate metallic needle cannula or moulded as an integral part of the main part.

The revolving part holds a plurality of needle cannulae in a circular alignment. Each individual needle cannula has distal pointed end adapted to penetrate the skin of a subject. The needle cannulae is located in a circular arrangement wherein each individual needle cannula has a first position in which the distal pointed end is retracted relative to the distal end of the magazine and a second position in which the distal pointed end projects from the distal end of the magazine to perform an injection.

The tube is arranged co-axial to a centre line of the main part, and the plurality of needle cannulae are provided the periphery of the revolving part and connected to the tube by a conduit embedded in the magazine. The conduit is preferably formed as a channel or system of channels moulded integral with the magazine or the conduit can be a separate tube embedded in the magazine during moulding. In this case the conduit and the tube can be made in one piece. The channel is shaped such that it guides the liquid drug flow from the centre line to the periphery of the magazine.

During use, the user rotates the revolving part thereby successively aligning one selected needle cannula with the terminating end of conduit guiding the liquid drug. The selected needle is brought into flow communication with the conduit by axial movement of the revolving part. This axial movement can be done against a bias of a spring during injection, or it can be done manually by the user prior to the injection.

In one example of the invention the conduit terminates in a direction perpendicular to the each individual needle cannula and thus perpendicular to the centre line of the magazine. The needle cannula is preferably mounted in a hub which is closed at its proximal end and provided with a side opening. This side opening can then be brought into communication with the perpendicular terminating end of the conduit by axially movement of the needle cannula. The axial movable hub carrying the needle cannula is thereby operating as a shut-off valve. The side opening can be a thorough-going bore in the hub, or it can be a moulded channel in the hub. Alternatively, the needle cannula can be bended such that the proximal end of the selected needle cannula can be brought into communication with perpendicular termination of the conduit when axial moved.

The conduit need not be formed as one lumen but can be made form a number of different lumens communicating to establish a flow. In one example, a first part of the conduit can be provided in the main part and a second part of the conduit can be provided in the revolving part. These two parts are then rotated into contact with each other to establish the flow communication. The first part in the main part is formed as one channel whereas the second part in the revolving part is formed as one separate channel leading to each individual needle cannula in the assembly.

In a different example the above conduit of the needle magazine terminates in a direction co-axially aligned with the selected needle cannula such that axial movement of the selected needle cannula penetrates the proximal end of the needle cannula through a septum and into the terminating part of the conduit.

In this example, the conduit preferably terminates in a chamber which is sealed by a septum. The needle cannulae revolves relatively to this chamber and thus when the selected needle cannula is in its injection position, the revolving part is shifted axially whereby the proximal end or non-patient end of the selected needle cannula penetrates through the septum and thereby establishes flow communication with the chamber.

In this example the needle cannula is attached to a hub such that a patient-end of the needle cannula protrudes distally and a non patient-end protrudes proximally. The hub, and thereby the needle cannula, is preferably moved axially by the axial movement of the revolving part, however, during injection the revolving part is moved further proximally such that the distal patient-end of the needle cannula extends beyond the revolving part.

When injecting, some users insert the needle cannula through the skin at an angle perpendicular to the skin while other users prefer to insert the needle cannula at a different angle. When not performing a perpendicular insertion, it is known that the smallest pain is observed if the part of the tip cut sharp enters the skin first to cut open the skin, which is automatically done when injecting with a perpendicular insertion. When injecting using a magazine as described it is therefore beneficial if the foremost cutting part of the tip slopes towards the centre of the magazine such that the most distal cutting part of the tip is located in the outer periphery of the magazine. In this position, when penetrating the skin at an angle it will be natural to hold the injection device and the magazine such that this foremost distal cutting part penetrates first.

DEFINITIONS

An "injection pen" is typically an injection apparatus having an oblong or elongated shape somewhat like a pen for writing. Although such pens usually have a tubular cross-section, they could easily have a different cross-section such as triangular, rectangular or square or any variation around these geometries.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

The term "Needle Cannula" is used to describe the actual conduit performing the penetration of the skin during injection. A needle cannula is usually made from a metallic material such as e.g. stainless steel and connected to a hub to form a complete injection needle also often referred to as a "needle assembly". A needle cannula could however also be made from a polymeric material or a glass material. The hub also carries the connecting means for connecting the needle assembly to an injection apparatus and is usually moulded from a suitable thermoplastic material. The "connection means" could as examples be a luer coupling, a bayonet coupling, a threaded connection or any combination thereof e.g. a combination as described in EP 1,536,854.

The term "Needle unit" is used to describe one single needle assembly carried in a container. Such container usually has a closed distal end and an open proximal end which is sealed by a removable seal. The interior of such container is usually sterile such that the needle assembly is ready-to-use. Needle units specially designed for pen injections systems are defined in ISO standard No. 11608, part 2, and are often referred to as "pen needles".

"Cartridge" is the term used to describe the container containing the drug. Cartridges are usually made from glass but could also be moulded from any suitable polymer. A cartridge or ampoule is preferably sealed at one end by a pierceable membrane referred to as the "septum" which can be pierced e.g. by the non-patient end of a needle cannula. The opposite end is typically closed by a plunger or piston made from rubber or a suitable polymer. The plunger or piston can be slidable moved inside the cartridge. The space between the pierceable membrane and the movable plunger holds the drug which is pressed out as the plunger decreased the volume of the space holding the drug. However, any kind of container—rigid or flexible—can be used to contain the drug.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which:

FIG. 7 show an exploded view of the needle magazine disclosed in FIG. 5-6

FIG. 8 show a cross sectional view through the line A-A in FIG. 6.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

Figure 1:
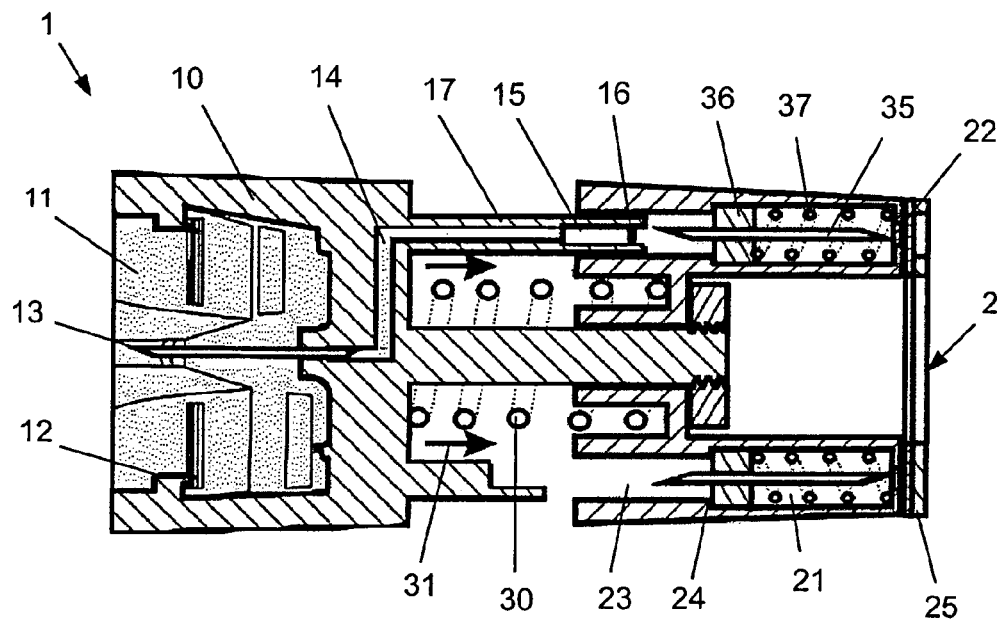
FIG. 1 show a cross sectional view of the needle magazine with the needle cannulae in the retracted position.

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" when referring to a needle magazine containing a number of needle cannulae, is meant to refer to the end of the individual needle cannula penetrating the patient whereas the term "proximal end" is meant to refer to the opposite end pointing away from the patient in a situation of use. In the appended figures these terms are used to the needle magazine as well.

FIG. 1 to FIG. 4 discloses an embodiment of a needle magazine 1. The needle magazine 1 comprises a main part 10 and a revolving part 20. The revolving part 20 is rotatable mounted to the main part 10 such that the main part 20 and the revolving part 20 can rotate relatively to each other.

The main part 10 is provided with a proximal located opening 11 having coupling means 12 for attaching the main part 10 to a non-shown injection device. The main part 10 is further provided with a tube 13 which can penetrate into the injection device when the magazine 1 is attached to the injection device. This attachment creates liquid flow communication with the liquid drug contained in the injection device, such that the liquid drug can flow from the injection device and into the tube 13.

The main part 10 is further provided with a conduit 14 which at its proximal end is co-axial with the tube 13 such that the liquid can flow from the injection device through the tube 13 and into the conduit 14.

Figure 3:
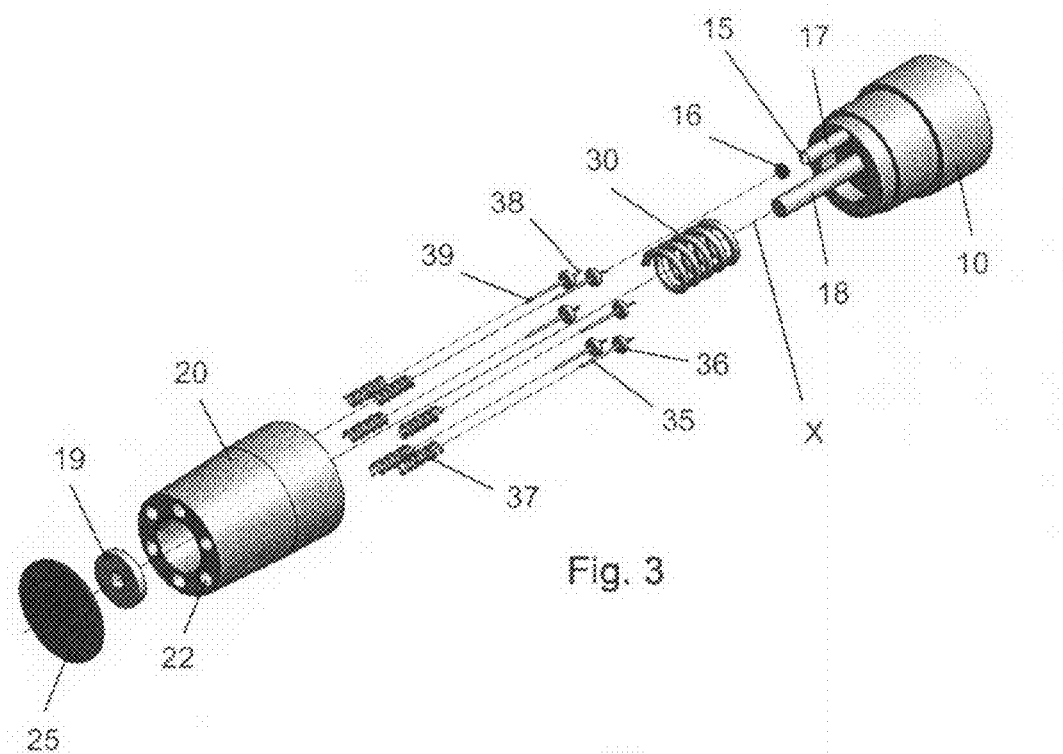
FIG. 3 show an exploded view of the needle magazine disclosed in FIG. 1-2.

The distal end of the conduit 14 terminates in a drug chamber 15 distally covered by a septum 16. This drug chamber 15 is located in a periphery extension 17 of the main part 10 as best seen in FIG. 3. With the needle magazine 1 attached to a well-known injection device the liquid drug will flow through the tube 13, into the conduit 14 and be present at the drug chamber 15 proximally to the septum 16.

The main part 10 of the needle magazine 1 is further provided with an extension 18 which terminates in a thread carrying a locking nut 19. Together this extension 18 and the locking nut 19 secure the revolving part 20 rotatable to the main part 10. The extension 18 is located co-axial with the centre line X of the needle magazine 1.

A magazine spring 30 is provided between the main part 10 and the revolving part 20. This spring 30 urges the revolving part 20 axially away from the main part 10 as indicated with the distally pointing arrows 31 in FIG. 1.

The revolving part 20 is provided with a plurality of needle cannulae 35 each of which is individually secured in a hub 36. Each individual needle cannulae 35 is further secured in an individual chamber 21 in the revolving part 20, in which chamber 21 each individual needle cannula 35 can travel axially.

Each chamber 21 has a distal opening 22 and a proximal opening 23. A needle spring 37 mounted in each chamber 21 urges each individual needle cannula 15 in the proximal direction such that the hub 36 abut a partition 24 internally in the chamber 21. This partition 24 is provided in a position in the chamber 21 where the distal end 39 of the needle cannula 35 lies proximally to the opening 22 i.e. the needle cannula 35 is in a retracted position. The distal opening 22 is preferably covered by a membrane 25 through which each needle cannula 15 can penetrate.

In use, when the needle magazine 1 is mounted on a not-shown injection device, the user rotates the revolving part 20 until a selected needle cannula 15 is axially aligned with the periphery extension 17 and thus the drug chamber 15. In this aligned position an injection is performed by pressing the most distal surface 2 of the needle magazine 1 towards the skin of the user. This forces the revolving part 20 to move proximally as indicated with the proximally pointing arrows 32 in FIG. 2. In this proximal position, the proximal end 38 of the selected needle cannula 35 penetrates through the septum 16 and into the drug chamber 15 whereas the distal end 39 of the selected needle cannula 35 penetrates through the membrane 25 and into the skin of the user thereby creating a liquid flow communication between the injection device and the subcutaneous region of the user.

Figure 2:
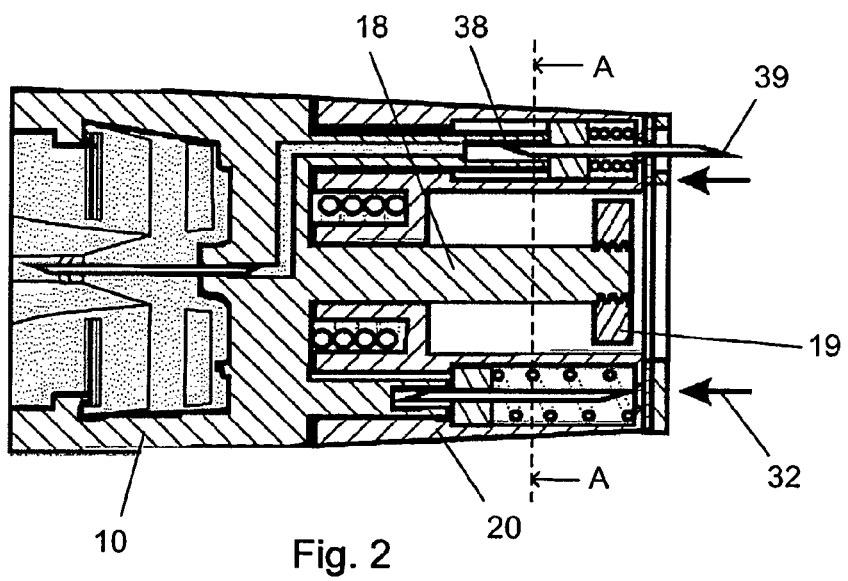
FIG. 2 show a cross sectional view of the needle magazine with the selected needle cannula in the injectable position.
Figure 4:
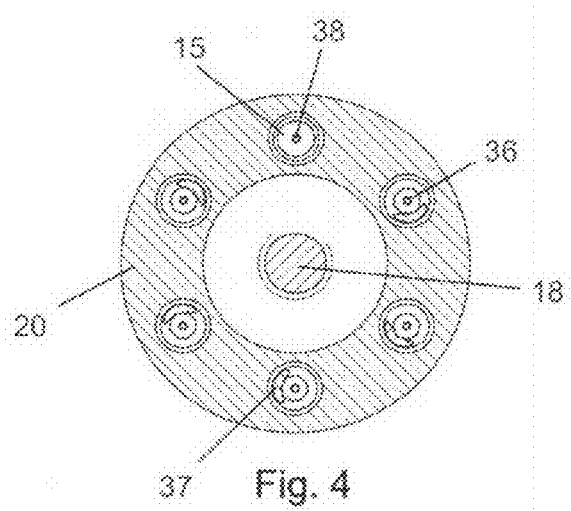
FIG. 4 show a cross sectional view through the line A-A in FIG. 2.

The injection situation is further disclosed in FIG. 4, which is a view along the line A-A of FIG. 2, i.e. during injection with the proximal end 38 of the selected needle cannula 35 (the upper in FIG. 4) penetrated into the drug chamber 15.

As disclosed in FIG. 2, the spring 30 is compressed as the revolving part 20 is moved proximally. The needle spring 37 within the chamber 21 carrying the selected needle cannula 35 actually in use is also compressed. When the user removes the most distal end 2 of the needle magazine 1 from the skin, the magazine spring 30 moves the revolving part 20 to its distal position and the needle spring 37 moves the selected needle cannula 35 to its retracted position.

Figure 5:
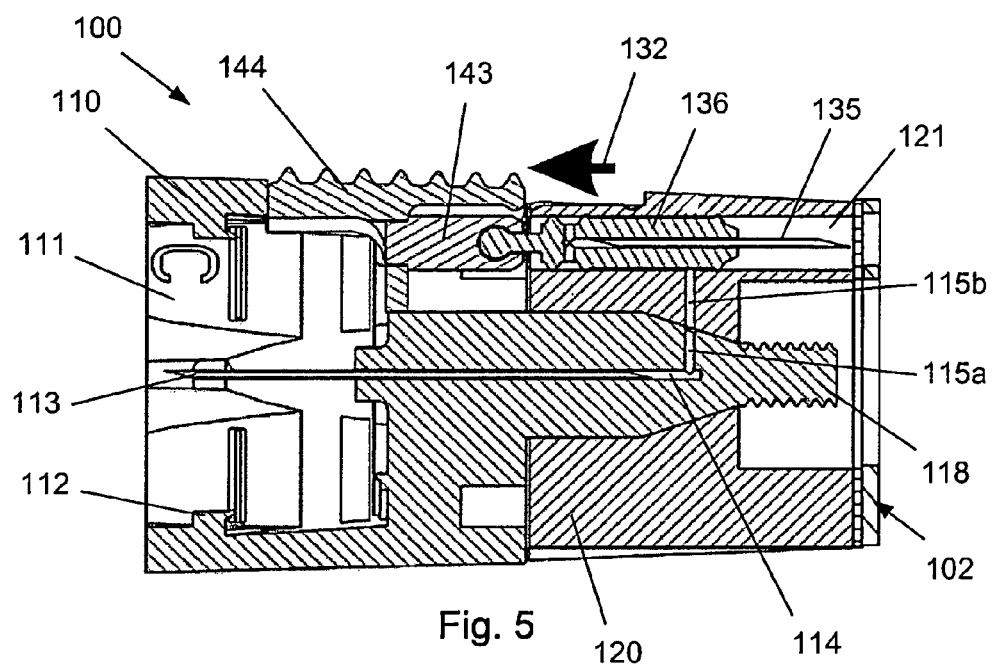
FIG. 5 show a cross sectional view of a needle magazine with the needle cannulae in a retracted position.

Alternatively the revolving part 20 can be moved proximally manually by the user prior to performing an injection as it is the case in the embodiment depictured in the FIG. 4 to FIG. 5.

This needle magazine 100 comprises a main part 110 and a rotatable revolving part 120. The main part 110 carries a centrally located tube 113 for penetrating the non-shown injection device to which the needle magazine 1 is to be attached. The proximal opening 111 is provided with coupling means 112 which as shown could be bayonet means.

The tube 113 terminates into a conduit 114 through which the liquid drug flow. This conduit 114 has an axial extending part extending axially from the tube 113 and a perpendicular part 115 extending perpendicular to the axial direction. The perpendicular extending conduit 115 has a first part 115a provided in the extension 118 and a second part 115b extending in the revolving part 120.

The extension 118, as in the first embodiment, secures the revolving part 120 rotatable to the main part 110 by threadedly engaging a not-shown nut member. Further as in the first embodiment, the extension 118 follows the centre line X of the needle magazine 100.

Each individual needle cannulae 135 has a distal end 139 for penetrating the skin of a user and a proximal end 138 which is secured inside the hub 136.

The hub 136 slides axially in the chamber 121 and is provided with a number of sealing surfaces 140, 141 which seals against the inner wall of the chamber 121. Between these sealing surfaces 140, 141, the hub 136 is provided with a through-going bore 142 which bore 142 are in flow communication with the lumen of the needle cannula 135 at its proximal end 138 such that liquid drug flowing into the bore 142 can enter the lumen of the needle cannula 135.

The hub 136 is further connected to a sliding element 143 which can be manually moved axially by a slider 144.

Figure 6:
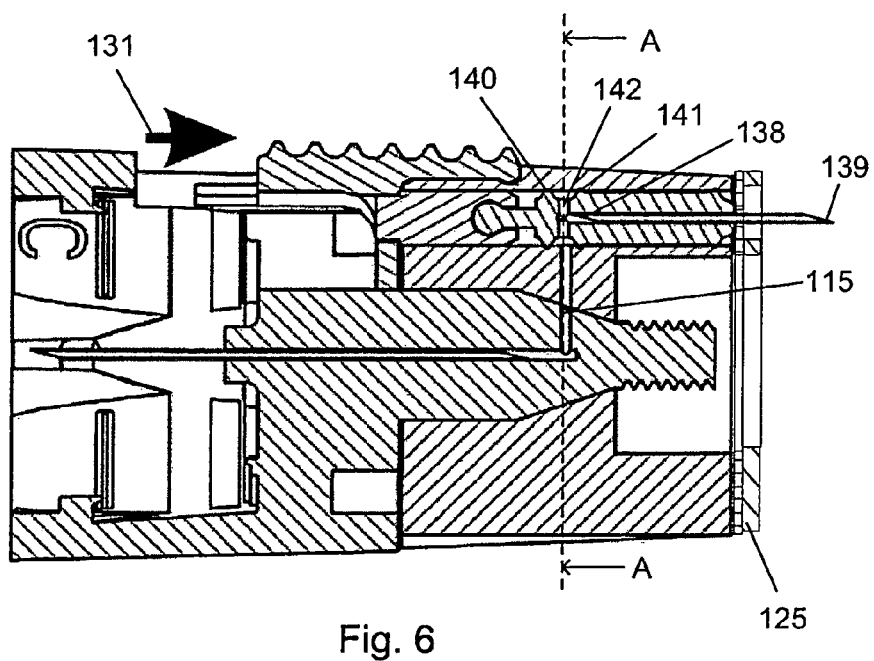
FIG. 6 show a cross sectional view of a needle magazine with the selected needle cannula in injectable position.

As best seen in FIG. 6, the user can slide the sliding element 143 together with the hub 136 and the needle cannula 135 in the distal direction by moving the slider 144 distally as indicated by the distally pointing arrow 131. By this movement, the through-going bore 142 is moved into radial alignment with the second part 115b of the perpendicular extending conduit 115, thereby creating liquid flow communication from the injection device, through the tube 113, further through the conduit 114, 115 (a+b), through the bore 142 and into the lumen of the needle cannula 135.

When the slider 144 is moved proximally as indicated by the proximally pointing arrow 132 in FIG. 5, the throughgoing bore 142 is moved out of radial alignment with the second part 115b of the perpendicular conduit 115 thereby shutting off the liquid flow communication.

As can be seen in FIG. 8, the extension 118 has one first part 115a of the perpendicular conduit 115 whereas there is one second part 115b for each individual needle cannula 135. In the shown embodiment this amounts to five second parts 115b.

Further the most distal end 102 of the needle magazine 100 can be made from a membrane 125 through which the needle cannulae 135 penetrates during injection. The membrane 125 is preferably made from a material through which the chambers 121 and the needle cannulae 135 can be sterilized and maintained sterile. Alternatively, each individual needle cannula can be contained in a flexible sterile envelope through which the cannula can penetrate.

Some preferred embodiments have been shown in the foregoing, but it should be stressed that the invention is not limited to these, but may be embodied in other ways within the subject matter defined in the following claims.

The invention claimed is:

1. A needle magazine attachable to an injection device containing a liquid drug, which magazine comprises:

A main part attachable to the injection device,

A revolving part which is rotatably mounted in relation to the main part,

The main part comprising at least one proximal pointing tube, which at least one proximal pointing tube is adapted to penetrate the injection device and create a liquid flow communication for the liquid drug contained in the injection device, The revolving part comprising a distal section provided with a plurality of needle cannulae in a circular alignment, each individual needle cannula comprising a distal pointed end adapted to penetrate the skin of a subject, and wherein each individual needle cannula has a first position in which the distal pointed end is retracted relative to the distal end of the magazine, and a second position in which the distal pointed end projects from a distal end of the magazine, wherein the at least one proximal pointing tube is provided co-axial to a centre line (X) of the magazine, and the plurality of needle cannulae are provided in a peripheral area of the revolving part of the magazine, wherein the magazine further comprises a conduit in liquid flow communication with the at least one proximal pointing tube and adapted to establish liquid flow communication between the at least one proximal pointing tube and each individual needle cannula in the plurality, and wherein rotation of the revolving part causes each individual needle cannula to in turn be successively aligned with the conduit whereupon axial movement of each individual needle cannula from the first position to the second position creates a liquid flow communication from the conduit and into each individual needle cannula.

2. A needle magazine according to claim 1, wherein the conduit terminates in a direction perpendicular to the each individual needle cannula.

3. A needle magazine according to claim 2, wherein each individual needle cannula is mounted in a hub which hub is closed at its proximal end and provided with a side opening.

4. A needle magazine according to claim 3, wherein the side opening in the hub is brought into communication with a termination of the conduit when the hub is moved axially.

5. A needle magazine according to claim 2, wherein a part of the conduit is provided in the revolving part of the magazine.

6. A needle magazine according to claim 1, wherein the conduit terminates in a direction co-axially aligned with a selected individual needle cannula.

7. A needle magazine according to claim 6, wherein the conduit terminates in a septum.

8. A needle magazine according to claim 7, wherein the selected needle cannula penetrates the septum when moved axially.

\* \* \* \* \*